(12) United States Patent
Wunderlich (10) Patent No.: US 9,023,047 B2
(45) Date of Patent: May 5, 2015

(54) METHOD AND SYSTEM FOR SHAVING BONE

(76) Inventor: Richard E. Wunderlich, Canton, GA (US)

(*) Notice: Subject to any disclaimer, the term of this patent is extended or adjusted under 35 U.S.C. 154(b) by 644 days.

(21) Appl. No.: 12/753,852

(22) Filed: Apr. 2, 2010

(65) Prior Publication Data

US 2011/0218536 A1 Sep. 8, 2011

Related U.S. Application Data

(60) Provisional application No. 61/166,693, filed on Apr. 3, 2009.

(51) Int. Cl.
*A61B 17/00* (2006.01)
*A61B 17/32* (2006.01)

(52) U.S. Cl.
CPC ........... *A61B 17/00* (2013.01); *A61B 17/32002* (2013.01); *A61B 17/320016* (2013.01)

(58) Field of Classification Search
CPC ............. A61B 17/32; A61B 17/32002; A61B 17/320016
USPC ..................... 606/79–85, 167, 170, 171, 177; 604/95.01, 523, 528
See application file for complete search history.

(56) References Cited

U.S. PATENT DOCUMENTS

| | | | | |
|---|---|---|---|---|
| 5,282,821 A | * | 2/1994 | Donahue | 606/170 |
| 6,451,022 B2 | * | 9/2002 | Dinger et al. | 606/85 |
| 2004/0147934 A1 | * | 7/2004 | Kiester | 606/80 |
| 2009/0105740 A1 | * | 4/2009 | Lee et al. | 606/177 |

* cited by examiner

*Primary Examiner* — Andrew Yang
*Assistant Examiner* — Diana S Jones
(74) *Attorney, Agent, or Firm* — John Doughty (57) ABSTRACT

A medical catheter extrusion forms a sheath around a wire. The extrusion is coupled to a steering and motivating handle. The handle is part of a housing that houses a motivation component fixed to the housing, a crankshaft, or similar eccentric component, couples to the motivation component, which is coupled to a proximal end of the wire. At the wire's distal end, a cutting tip with canted teeth couples to the wire. The cutting tip is capable of cutting bone when moving axially toward the catheter extrusion but glides across the bone without cutting it when moving axially away from the catheter extrusion. The motivation component can be a motor or buttons or a trigger, that couple to the wire and converts manual movement into reciprocating motion of the flexible shaft. The shaft's reciprocating motion moves the flexible and steerable shaft back and forth to move the cutting tip.

8 Claims, 9 Drawing Sheets

FIG. 1
(Existing 2-Way Steering)

FIG. 2
(Existing 2-Way Steering)

Right Hand Steering Motion Achieved By Applying Tension To Wire 6R

FIG. 3

FIG. 5
(3-Way Steering)

Steering Planes

METHOD AND SYSTEM FOR SHAVING BONE

CROSS REFERENCE TO RELATED APPLICATION

This application claims priority under 35 U.S.C. 119(e) to U.S. provisional patent application No. 61/166,693 entitled "Method and system for shaving bone using a catheter," which was filed Apr. 3, 2009, and is incorporated herein by reference in its entirety. This application also incorporates by reference U.S. patent application Ser. No. 12/132,102 in its entirety.

BACKGROUND

Figure 1:
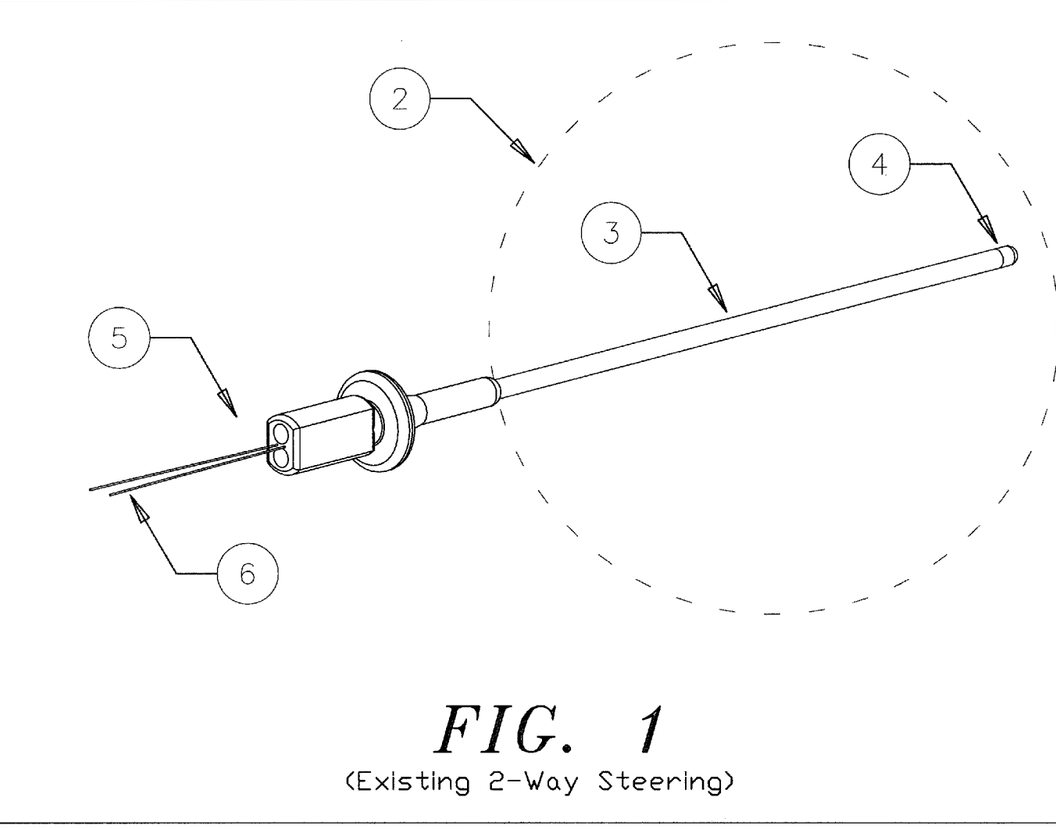
FIG. 1 illustrates a catheter extrusion for facilitating two-way steering of a distal end.
Figure 2:
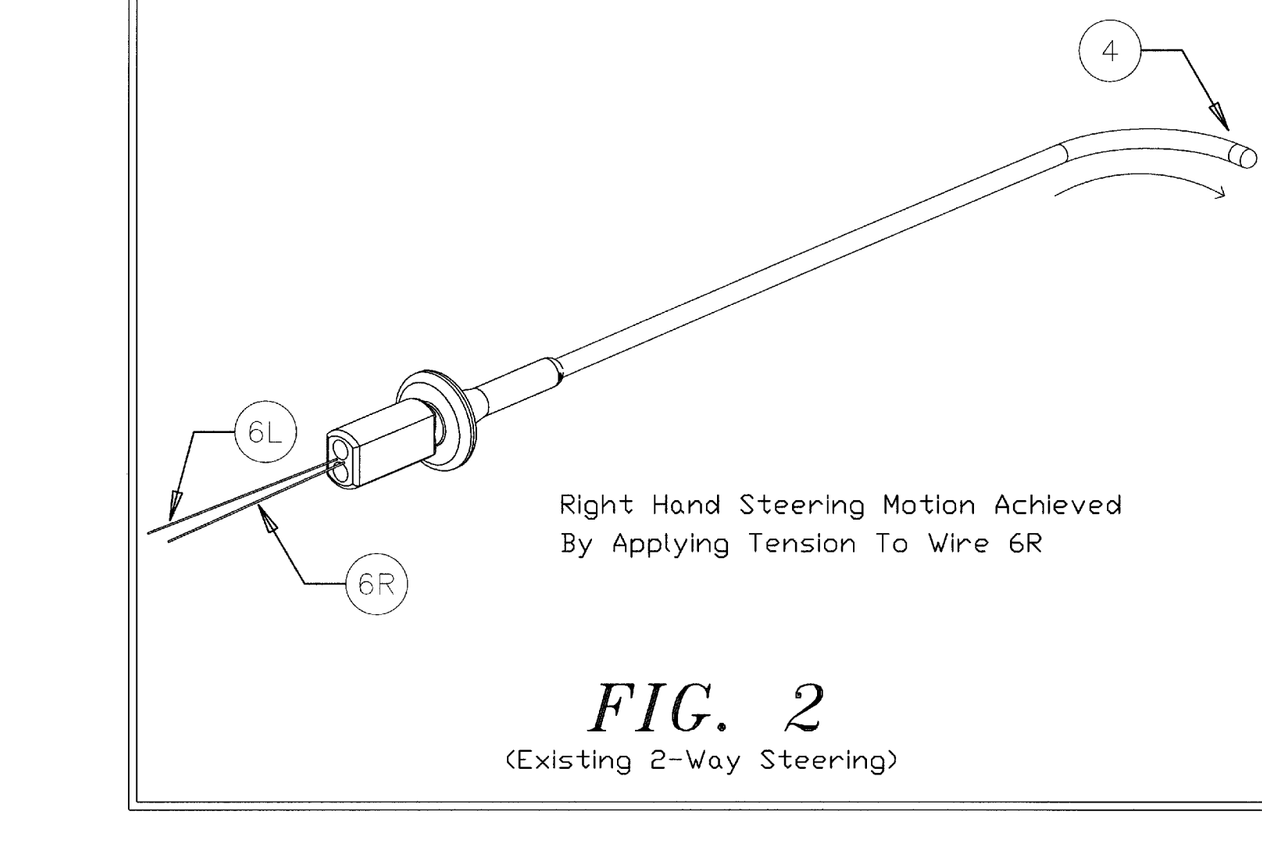
FIG. 2 illustrates the distal end of a catheter extrusion deflected in a rightward direction.

Catheters used in the medical industry, such as catheter products produced by Myelotec, Inc. for example, steer a distal end by manipulating stainless steel wires anchored into the distal tip of a plastic extrusion. FIG. 1 illustrates a catheter assembly 2 comprising extrusion 3 and distal end 4. Distal end 4 may include a lens and light carrying means, such as optical fiber, that facilitates a user viewing tissue and organs of a human, or animal, body. Applying tension to the proximal end 5 of either wire 6 causes distal end 4 of extrusion 3 to deflect in the direction of the wire 6, to which tension was applied, relative to the centerline of extrusion 3. For example, FIG. 2 illustrates that tension has been applied to rightmost steering wire 6R causing distal end 4 to deflect to the right. Similarly, applying tension to steering wire 6L (the figure does not illustrate this scenario for clarity) would cause distal end 4 of extrusion 3 to deflect to the left, or the opposite direction as that shown in the figure, but in the same plane as the movement depicted in FIG. 2.

Figure 3:
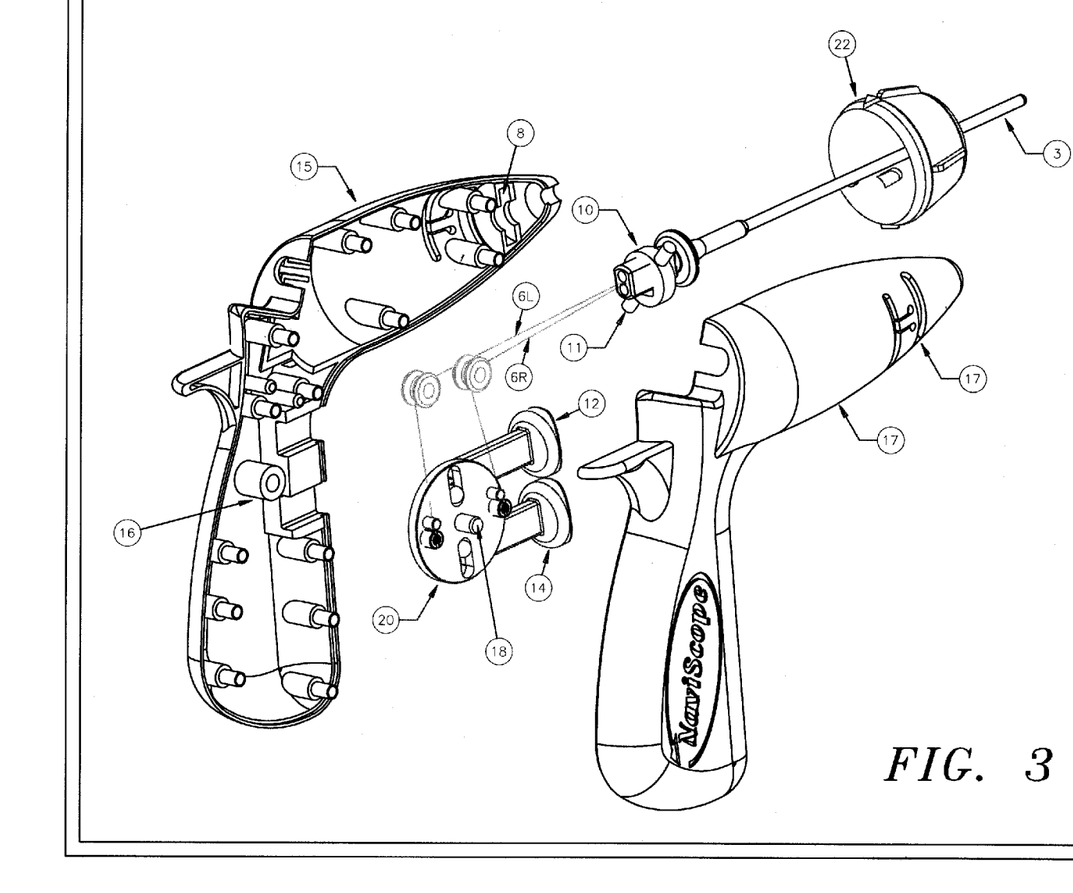
FIG. 3 illustrates a Naviscope steerable catheter pistol grip assembly for facilitating two-way steering of a catheter extrusion distal end.

In a two-wire configuration, such as the Naviscope® steerable catheter product line sold by Myelotec, Inc., a user may steer in only one plane at a time. Although the steering plane may be rotated 90° via a steering yoke and external collar from horizontal to vertical (See FIG. 3), compound movements, such as left-to-right sweeps while pointing downward, cannot be performed using two steering wires. As shown in FIG. 3, yoke bearing 8 receives rotation yoke 10 and rotation pin 11 protrudes through rotation slot 13. When housing halves 15 and 17 are mated together, collar 22 slides over the end of the mated housing halves and engages pin 11. Thus, a user gripping collar 22 can rotate extrusion 3 by turning collar 22. The extent of slot 13 limits the amount of rotation so that wires 6R and 6L remain untangled. When steering bearing 16 has received axle 18 of steering wheel 20, manipulating buttons 12 and 14 causes the distal end of extrusion 3 to deflect correspondingly. For example, pressing button 14 induces tension in steering wire 6R, which causes the distal end to deflect to the right as described above in connection with the discussion of FIG. 2. Similarly, pressing button 12 would induce tension in steering wire 6L and cause the distal end to deflect to the left.

Figure 7A:
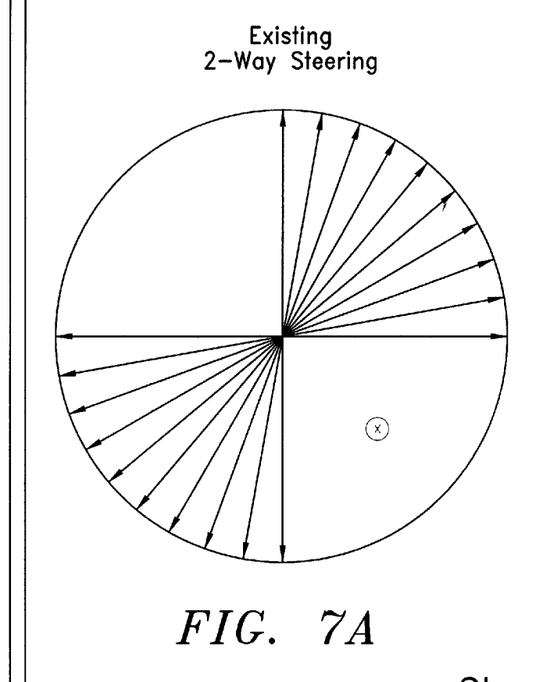
FIG. 7A illustrates the possible steering planes of a two-wire steered extrusion.

A user may be able to rotate the steering plane (via collar 22) and re-point distal end 4 toward a desired location within a body, but only if the desired location falls within the area depicted in FIG. 7A. Should the location fall outside the possible steering planes (the point depicted with an X in FIG. 7A e.g.) the user must rotate housing halves 15 and 17 for viewing. However, since the optical fiber is attached to the housing, the image seen will be tilted with respect to the previous orientation of the image. Thus, there is a need for a catheter steering device that can steer a distal end of a catheter extrusion in multiple planes rather than one plane without causing image tilt as occurs when the distal end is rotated via the housing halves rather than being steered. Also, a need occasionally arises to cut bone without cutting a patient.

DETAILED DESCRIPTION

Figure 4A:
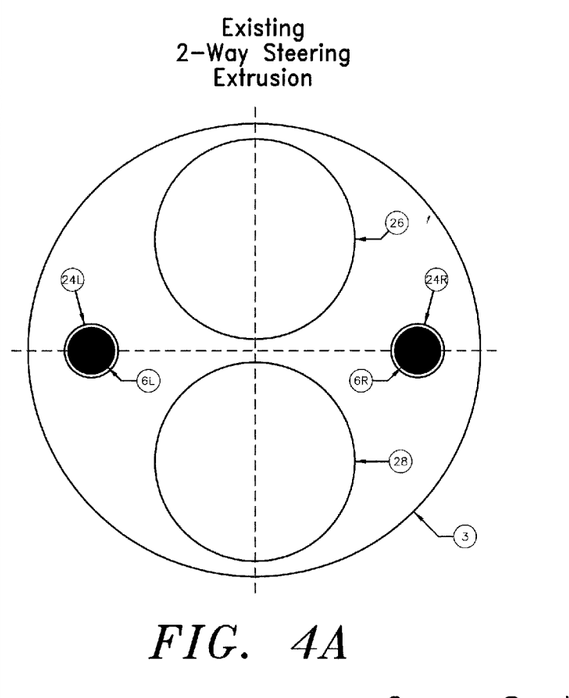
FIG. 4A illustrates a sectional view of a catheter extrusion for facilitating two-way steering.
Figure 4B:
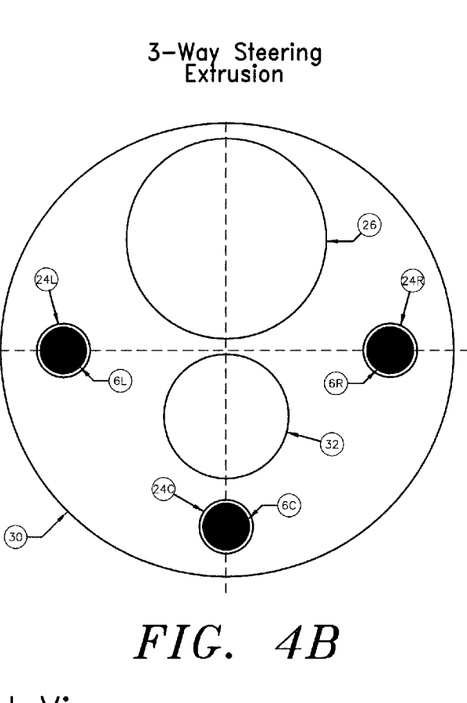
FIG. 4B illustrates a sectional view of a catheter extrusion for facilitating three-way steering.

Turning now to the figures, FIG. 4 illustrates an aspect by comparing a sectional plan view of a catheter extrusion 3 for two way steering that uses two steering wires in FIG. 4A with a sectional plan view in FIG. 4B of a catheter that facilitates multiway steering using three steering wires. As discussed in connection with previous figures, steering wires 6R and 6L enter extrusion 3 through respective steering wire lumens 24R and 24L. Operational lumens 26 and 28 are shown larger than the steering wire lumens 24R and 24 L because they facilitate operational items such as, for example, fiber for passing light to and from a distal end of extrusion 3 and possibly a tube carrying air or wires for manipulating a cutter for abscising tissue. In the two steering wire system facilitated by the section of extrusion 3 shown in FIG. 4A, lumens 26 and 28, although of equal diameter, are sized so that they equitably share the sectional area of the section shown in the figure with lumens 24L and 24R.

Turing now to FIG. 4B, extrusion 30 defines center steering wire lumen 24C. Lumen 24C receives and routes steering wire 6C, which transfers force from a hand grip to a distal end of extrusion 30, causing the distal end to move in a plane orthogonal to the plane within which wires 6L and 6R cause movement. Since only center wire 6C causes motion in what will be referred to herein as a second plane (the first plane being the plane in which tension in wires 6L and 6R cause motion), the motion in the second plane will occur in only one direction away from a relaxed, or straight-extending, position of the distal end of extrusion 30. To accommodate the extra area of the illustrated section of extrusion 30, the extrusion defines smaller lumen 32 rather than lumen 28, which is similarly sized as lumen 26. Extrusion 30 defines the size of smaller lumen 32 to make room for the addition of steering wire lumen 24C while still being large enough in diameter to accommodate items described above, such as light fiber or possibly wires for manipulating a biopsy tissue sample: collector. Alternatively, a designer/manufacturer may increase the size of the extrusion from, for example, 3.0 mm to 3.3 mm, to facilitate the extra operational lumen(s) of suitable size.

Figure 5:
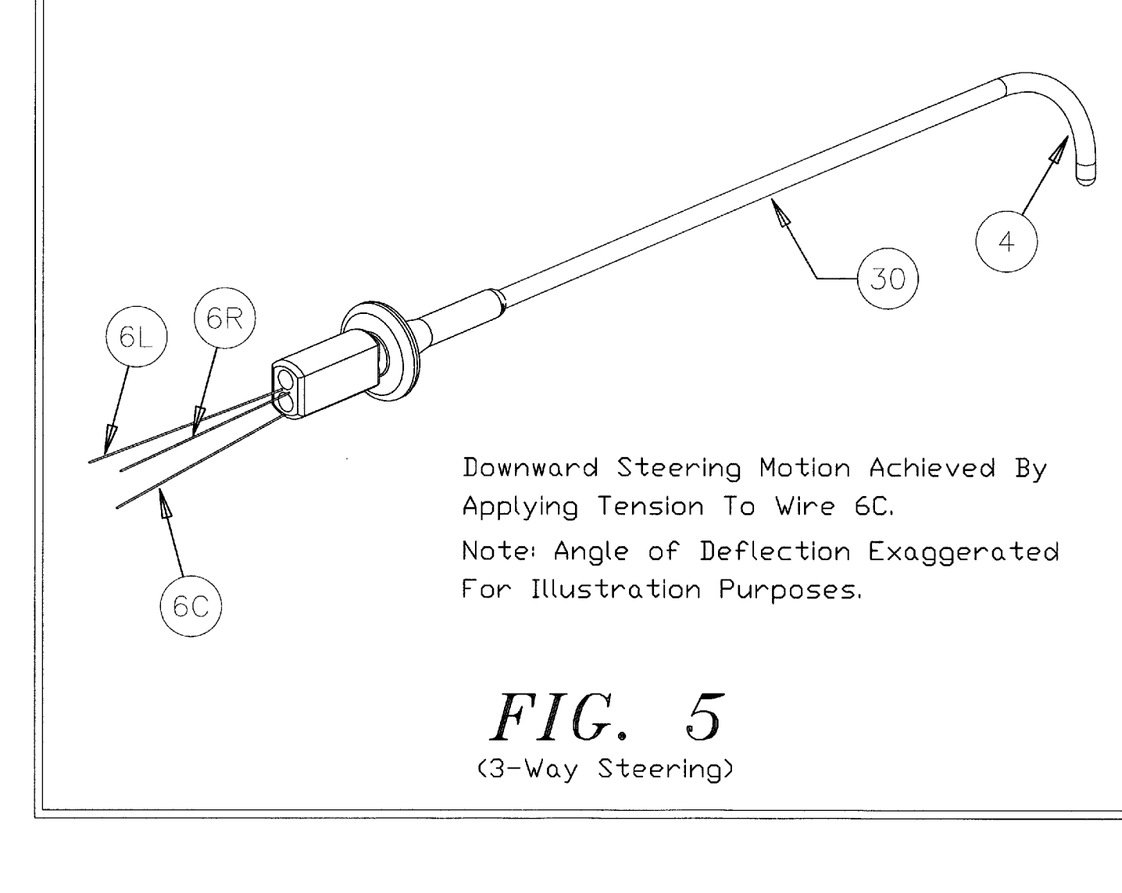
FIG. 5 illustrates a catheter extrusion for facilitating three-way steering of a distal end.

Turning now to FIG. 5, the figure illustrates steering wires 6L, 6R and 6C being routed through corresponding steering wire lumens defined by extrusion 30. Tension in center steering wire 6C causes distal tip to deflect downward as shown in the figure. It will be appreciated that a fourth steering wire and corresponding steering wire lumen could be added to cause motion of distal end 4 in the up direction as well as the down direction.

Figure 6:
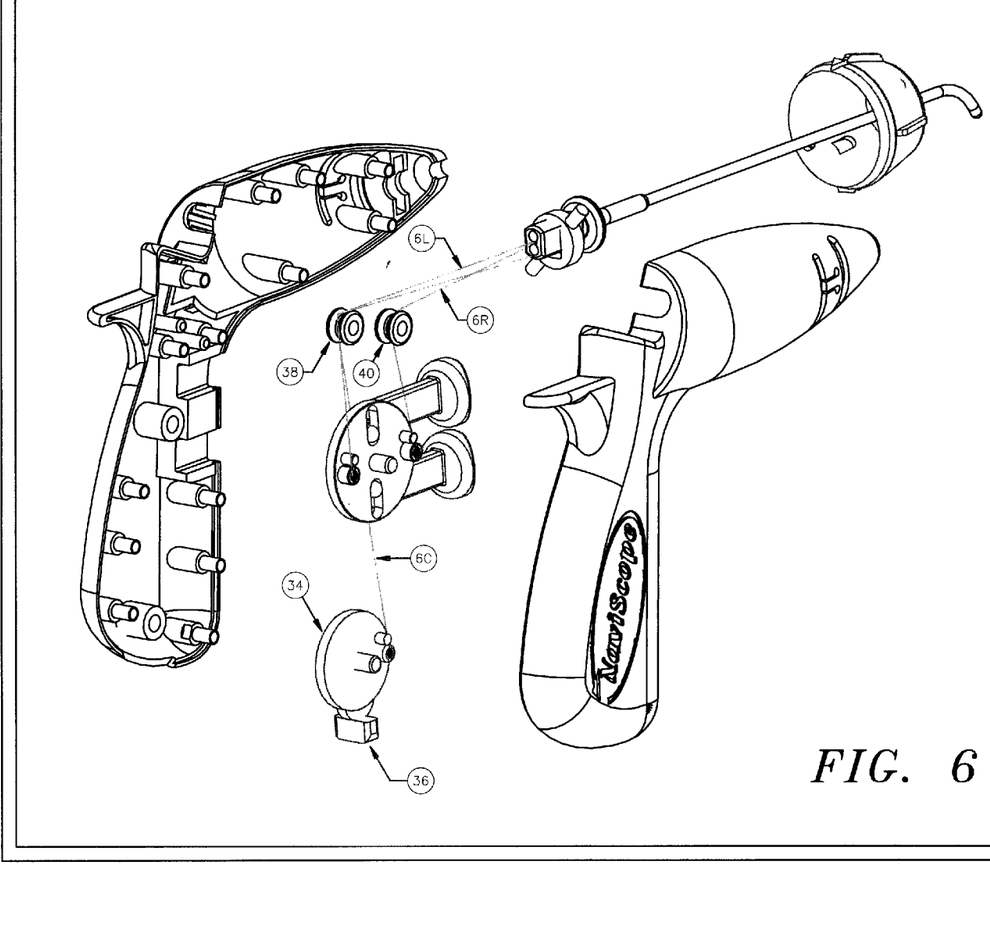
FIG. 6 illustrates a Naviscope steerable catheter pistol grip assembly modified to facilitate three-way steering of a catheter extrusion distal end.

Turning now to FIG. 6, the figure illustrates a second plane steering dial 34 added to the Naviscope steerable catheter assembly that is shown in FIG. 3. Manipulation of steering tab 36 in the clockwise direction causes tension in center steering wire 6C, which causes motion in the down direction of distal tip 4. Center steering wire 6C shares guide wheel 38 with left steering wire 6L, which is already present in a two wire steering system, thus reducing the number of addition parts to facilitate three wire steering as compared to two wires steering. Steering wire 6R continues to use guide wheel 40 as it does in a two wire steering arrangement.

Figure 7B:
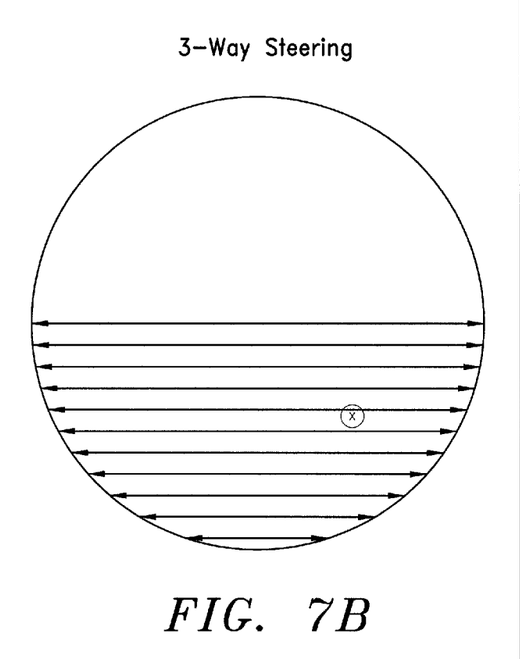
FIG. 7B illustrates possible planes of a three-way steered extrusion.

Turning now to FIG. 7B, for the figure shows that, the point depicted with an X can be viewed in proper orientation by first deflecting distal end 4 downward, and then steering left to right as normal. Thus, image orientation does not change as a user steers extrusion 3 as compared to the image orientation change that occurs when a user rotates the steering handgrip housing in a two-wire steering system.

Figure 8:
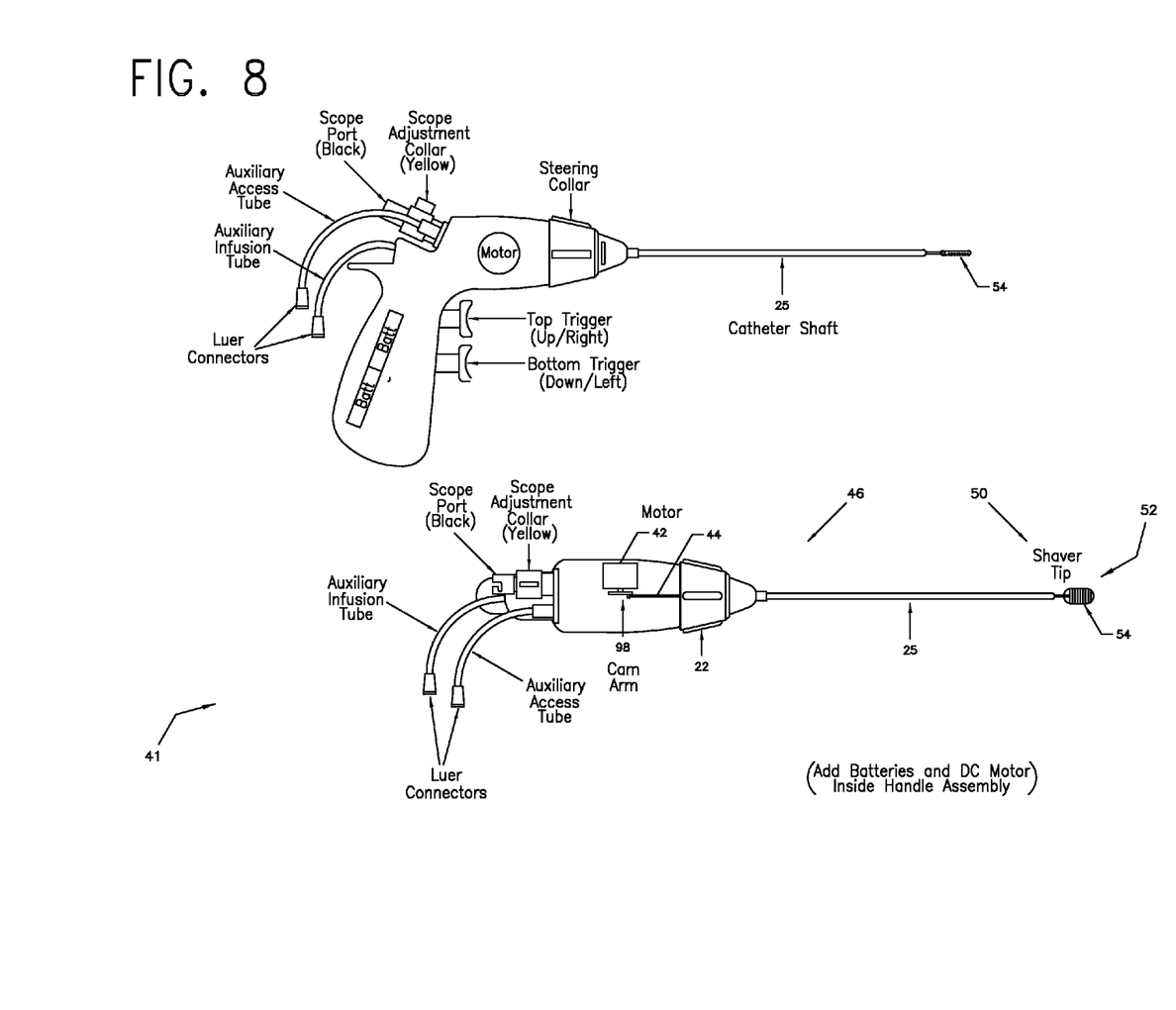
FIG. 8 illustrates a Naviscope steerable catheter pistol grip assembly modified to motivate a flexible shaft in a back and forth motion through a catheter to shave bone.

Turning now to FIG. 8, the figure illustrates a steerable catheter handle grip housing 41 as described above. Housing 41 provide a structure for mounting an electric motor 42, or similar motivating component. A user may turn on or off the motor by using a button mounted on the housing, or squeezing a switch grip that operates electrical switch contacts. Other than a motor, manually operated buttons on the outside of housing 41 may cause an output shaft to rotate when a user manipulates the buttons. Motor 42 couples to flexible shaft 44, preferably a wire, which projects through shaver shaft catheter 25. Catheter 25 slidingly covers wire 44, acting as a sheath, so the wire can slide back and forth (substantially coaxially) inside the catheter. Wire 44 extends through proximal end 46 of catheter 25. It will be appreciated that proximal end 46 of catheter 25 may terminate where the catheter enters steering collar 22. Or, catheter 25 may extend through collar 22 and terminate near motor 42. If catheter 25 extends through collar 22, the catheter should terminate far enough away from motor 42 to permit clearance for movement of conversion means 48. Conversion means 48 may be a cam, a crank, a lever, a wheel with a attachment screw at a point on the perimeter of the wheel, or other means, that can convert rotational movement of an output shaft from motor 42 into reciprocating motion, or back and forth motion.

An example of the wheel and attachment point is similar to the operation of a steam locomotive's drive wheel in reverse. In a locomotive scenario, reciprocating motion of the piston pushing a rod attached near the perimeter of the wheel converts into rotational motion of the drive wheel. In the bone shaver apparatus described herein, the turning wheel driven by the motor can couple to the flexible shaft at an attachment point near the perimeter of the wheel. Thus the wheel and attachment point convert rotational motion of the wheel into reciprocating, or back and forth, motion of the flexible shaft.

Alternatively, in another aspect, a trigger hinged from housing 41 to move similar to how a gun trigger moves may be used to cause shaft 44 to move back and forth axially with respect to an axis of catheter shaft 25. It will be appreciated that the closer catheter 25 terminates with respect to conversion means 48, the more flexible wire 44 can be before buckling of the shaft occurs.

Shaft 44 exits catheter 25 at a distal end (distal and proximal terminology refers to location relative to housing 41). At distal end 50, a cutting portion comprising a cutter, or shaver tip 52, couples to wire 44. Clearance 54 between the shaver tip 52 and the extent of catheter 25 where it ends should be enough to prevent interference between the tip and the catheter when conversion means 48 has moved tip 52 back towards proximal end 46 at the maximum displacement of the conversion means.

Conversion means 48 places wire 44 in tension as it moves in a back direction (toward the proximal end). This can transfer substantial force axially with respect to the wire to shaver tip 52. However, when conversion means 48 moves in a forward, or forth, direction (toward the distal end), wire 44 cannot transfer much force to tip 52 because the wire is placed in a compression condition. Thus, shaver tip 52 is designed to impart cutting force to a bone when moving in a backward direction and not impart much force in the forward direction.

Figure 9:
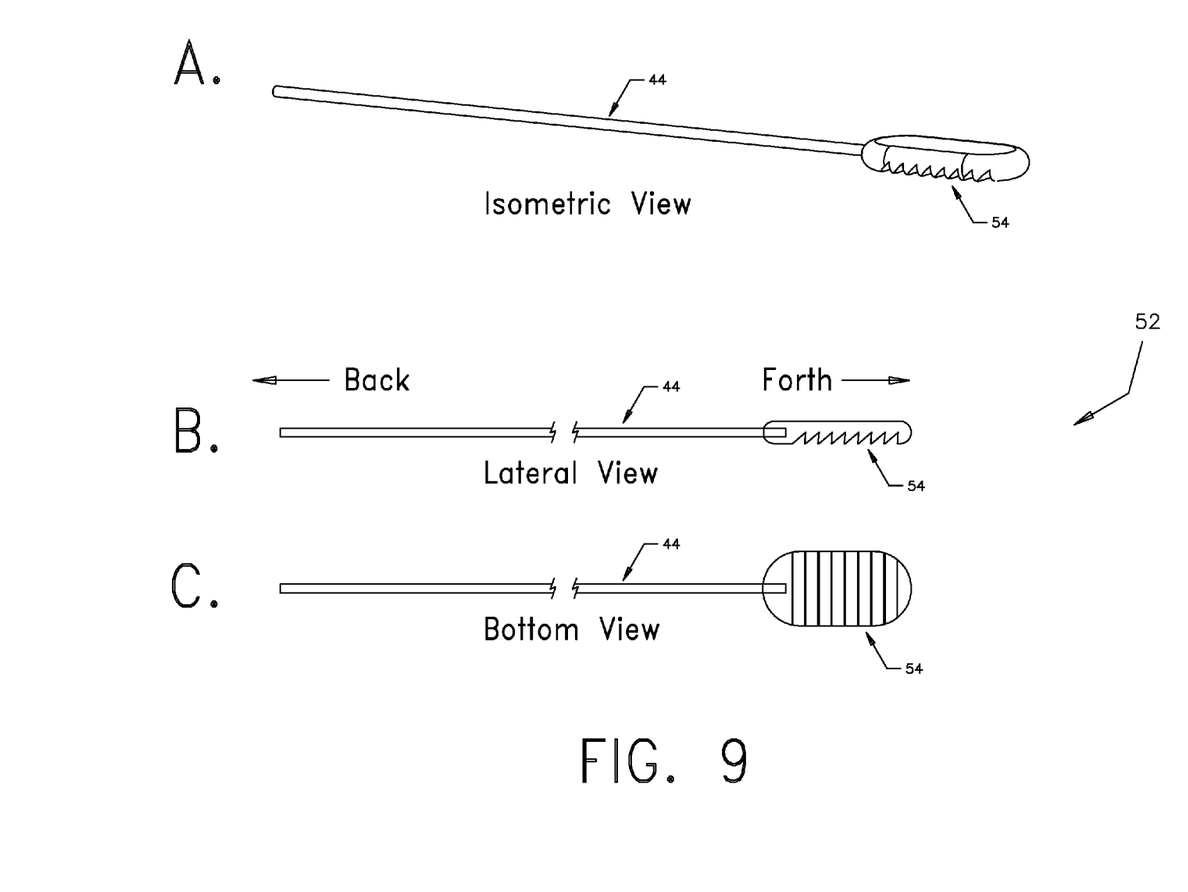
FIG. 9 illustrates a bone shaving implement with canted teeth projecting from a cutter coupled to a flexible shaft.

Turning now to FIG. 9, the figure illustrates different views of shaver tip 52. View A and view B illustrate canted cutting teeth 56. The cant angle is toward the direction of backward motion of wire 44 shown in FIG. 8. Thus, when wire 44 moves in the backward direction, canted teeth 56 cut bone. But, when wire 44 moves in the forward direction, since teeth 56 angle away from the direction of motion, the teeth essentially glide over the bone, thus not imparting much, if any, resistive force that the shaft, or wire, which is in a compression state, need overcome. Although wire 44 typically is sheathed in catheter 25, trying to cut bone when tip 52 moves in the forward direction would tend to cause buckling which could lead to binding of the wire in the catheter. More importantly, even with minimal distance between the end of the proximal end of catheter 25 and the conversion means, more than a very minimal compression of wire 44 between the extent at the proximal end of the catheter and the attachment point where wire 44 attaches to the conversion means 48 would cause buckling of the wire in that unguided portion. If the wire buckles in the unguided portion between the extent of catheter 25 and conversion means 48 rather than staying relatively rigid, the motion of the conversion means does not translate into forward motion at tip 52. And, if tip 52 does not move in a forward motion after moving in a backward motion, it will not perform cutting again because motion on the conversion means in the backward motion would not move the cutting tip, but would only straighten the buckled wire portion. Thus, canted teeth 54 on cutting tip 52 provide cutting in the backward motion of wire 44 while allowing the tip to slide over the just-cut bone when moving in the forward direction.

It will be appreciated that cutting tip 52 may be manufactured separately from wire 44 and coupled to the wire by welding, clamping, gluing, pressing, stamping, or other similar methods. Alternatively, cutting tip 52 may be formed into the end of wire 44 by pressing, or smashing, the distal end of the wire into an oblong shape and then machining canted teeth 54 in to the formed oblong shape.

It will also be appreciated that the electric, motor can be powered by batteries housed in the housing handle and electrically coupled to the motor in series with the switch means discussed above. Or, an external power supply can provide power to the motor through a plugged connection mounted on the housing with the switch electrically in series with the motor. In addition, a trigger, or a squeeze grip switch can comprise a potentiometer means, or other means for regulating power delivery from the power source to the motor, so that a user operating the bone shaving apparatus can vary the speed of the cutting tip in proportion to pressure on the trigger or grip.

What is claimed is:

1. An apparatus for cutting, comprising:
a flexible shaft configured to couple to a conversion means at a proximal end of the shaft, wherein a catheter slidingly covers the shaft substantially from the proximal end of the shaft to a distal end of the shaft;
wherein a cutting portion couples to the flexible shaft past a distal end of the catheter, and wherein the cutting portion is configured to cut bone when the flexible shaft moves it toward the catheter from which it projects;
wherein the catheter is steerable in multiple planes, and wherein the cutting portion can cut while being steered in the multiple planes;
a housing that includes a support;
a motivation component fixed to the support, the motivation component including an output;
a conversion means coupled to the output of the motivation component capable of converting an input motion to a backward and a forward motion, wherein the conversion means couples to the flexible shaft at an attachment point so that the conversion means converts rotational motion of into reciprocating motion of the flexible shaft at its proximal end; and
wherein the conversion means converts an input motion into a reciprocating motion of the flexible shaft along a longitudinal axis of the flexible shaft.

2. The apparatus of claim 1 wherein the cutting portion includes a cutter that is configured to slide across bone without cutting it when the cutter moves in response to the forward motion caused by the conversion component.

3. The apparatus of claim 1 wherein the cutting portion is configured to cut bone.

4. The apparatus of claim 1 wherein the cutting portion defines teeth angled in the direction of the backward motion.

5. A system for cutting, comprising:
a housing that includes a support;
a motivation component fixed to the support, the motivation component including an output;
a conversion component coupled to the output of the motivation component capable of converting an input motion from the output into a backward and a forward motion;
a flexible shaft coupled to the conversion component at a proximal end of the shaft, wherein a catheter slidingly covers the shaft substantially from the proximal end of the shaft to a distal end of the shaft;
wherein a cutting portion couples to the shaft past a distal end of the catheter and;
wherein the catheter is steerable in multiple planes, and wherein the cutting portion can cut bone while being steered in the multiple planes; and
wherein the conversion component converts the input motion from the output of the motivation component into the backward and forward motion along a longitudinal axis of the flexible shaft, wherein the conversion component includes an eccentric wheel hub that converts rotational motion of the motivation component to the backward and the forward motion.

6. The apparatus of claim 5 wherein the cutting portion includes a cutter that is configured to slide across bone without cutting it when the cutter moves in response to the forward motion caused by the conversion component.

7. The apparatus of claim 5 wherein the cutting portion is configured to cut bone.

8. The system of claim 5 wherein the cutting portion defines teeth angled in the direction of the backward motion.

* * * * *